United States Patent [19]

Rudisill et al.

[11] Patent Number: 4,831,332
[45] Date of Patent: May 16, 1989

[54] CONTINUOUS ADJUSTING APPARATUS FOR DETECTING GASEOUS IMPURITIES WITH A CORONA DISCHARGE

[76] Inventors: Michael E. Rudisill, 412 Whispering Hill Dr., Hendersonville, N.C. 28739; Glenn R. Reddington, 223 Wimbledon Lake Dr., Plantation, Fla. 33324; John E. Kennedy, 340 Cascade Rd., Pisgah Forest, N.C. 28768

[21] Appl. No.: 933,993

[22] Filed: Nov. 24, 1986

[51] Int. Cl.$^4$ .............................................. G01N 27/62
[52] U.S. Cl. .................................... 324/455; 324/464; 340/632; 361/233
[58] Field of Search ................ 324/464, 455; 340/632; 361/230, 233; 363/21, 19

[56] References Cited

U.S. PATENT DOCUMENTS 4,488,118 12/1984 Jeffers et al. ......................... 324/455
4,510,562 4/1985 Maeba ..................................... 363/19

Primary Examiner—A. D. Pellinen
Assistant Examiner—Morris Ginsburg

[57] ABSTRACT

An apparatus for continuously adjusting the corona discharge currrent of a pair of electrodes exposed to an atmosphere of gaseous impurities, particularly halogen. The device consists of a power supply to cause a corona current to flow in a pair of electrodes in series with a summing resistor. Any change in the gaseous impurities which causes a change in the corona current is sampled in the resistor, detected, delayed, amplified and fed back in proper phase to the control element of the power supply to cause the corona current to remain constant. During the finite delay time the change in corona current causes an audible alarm to sound until the corona current is restored to the new level of impurity concentration. The corrective action is continuous for any level of impurity concentration.

1 Claim, 4 Drawing Sheets

CONTINUOUS ADJUSTING APPARATUS FOR DETECTING GASEOUS IMPURITIES WITH A CORONA DISCHARGE

BACKGROUND OF THE INVENTION

The present invention relates generally to apparatus for detecting impurities in a gaseous atmosphere with a corona discharge and more particularly, to a continuously adjusting corona current source.

Apparatus for detecting gaseous impurities, such as halogens, in atmospheres with a continuous corona discharge are known in the prior art. Such devices are known to be sensitive indicators of the presence and concentration of gaseous impurities. Of special interest is the fact that the corona discharge current level diminishes with increasing concentration of halogen gases, since halogen gases possess positive ions, which combine with the negative ozone ions within the corona discharge to decrease the space charge current flow. The recombinations of ions is dramatic in that a large current change occurs for a small concentration of gaseous impurities. As a result of this phenomenon, these devices are capable of detecting halogen gases in very low concentrations. Likewise, the ability to maintain an optimum level of corona current within a constantly changing background level of impurities is highly desirable. To maintain this optimum corona current flow over a long period of time regardless of slowly varying background levels, humidity, air flow, sensing tip variations, electronic components drift, contamination and human adjustment errors requires a continuously adjusting apparatus.

The typical prior art devices used some automatic means to establish an initial adjustment, independent of manual methods, and then assumed this condition to remain stable; or else made timely periodic recalibration setups at fixed intervals.

Since the prior art states that the devices are inherently unstable requiring troublesome frequent recalibration, there were many attempts to resolve the problem.

SUMMARY OF THE INVENTION

The principal object of this invention is to overcome the deficiencies of heretofore known methods of halogen gas leak detectors by providing a novel and improved continuously adjusting apparatus using a servo feedback control technique to cause the corona discharge current to be maintained at an optimum sensitive level.

A more particular objective of the invention is to provide a means of continuously adjusting the corona current in either direction to maintain optimum corona discharge currents while alerting the operator to any corrective change in the corona current which indicates a change in the halogen concentration.

The servo feedback control technique used in this invention samples the corona discharge current in a summing resistor placed in series with the corona discharge current. The resulting voltage is compared to a reference and applied to the high voltage power supply feedback winding to maintain an empirically determined optimum corona current. Any subsequent change in the corona current generates an error voltage at the summing resistor which is applied to the feedback winding of the power supply in proper phase to cause the corona current to remain constant. Likewise, the error voltage is amplified and applied to threshold detector circuits which signal an increase or a decrease in the corona current as a change in the gaseous impurity concentration of the atmosphere.

BRIEF DESCRIPTION OF THE DRAWINGS

These and other objectives, features, and elements of the invention will be more readily apparent from the following detailed description of the drawings in which.

DESCRIPTION OF THE PREFERRED EMBODIMENT

Figure 1A:
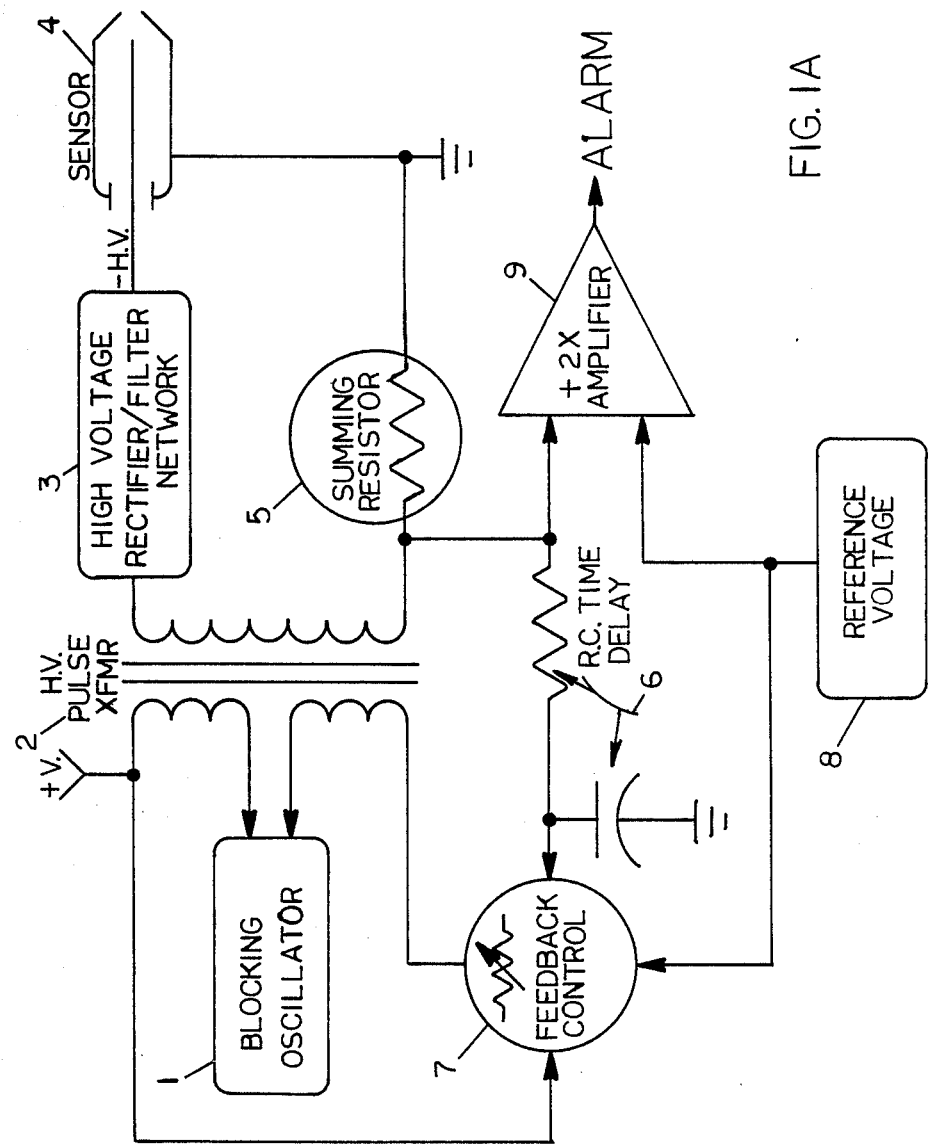
FIG. 1A is a simplified schematic of the basic servo feedback control embodiment of the invention.

With reference to FIG. 1A of the simplified schematic, the principal object of this invention is explained as follows: A high voltage pulse type transformer 2 is connected to a conventional blocking oscillator 1 with a feedback control 7. The generated pulses in the transformer secondary are rectified and filtered in the network 3 to provide a highly negative voltage to the corona generating sensor 4 which in series with the summing resistor 5 completes the corona discharge current path to the transformer secondary. The level of the corona current is initially established by a bias current in the feedback winding of the blocking oscillator 1. This bias current is controlled by the feedback control circuit 7 after a time delay 6 and comparison of the reference voltage 8 with the voltage at the summing resistor 5. After the initial setup, any changes in the corona current through the summing resistor 5 are sensed as an error voltage when compared to the reference voltage 8. This error voltage is applied through the feedback control 7 to the feedback winding of the blocking oscillator 1 in proper phase to cause a correction of the corona discharge current to the original value. The RC time delay 6 applies the correct timing to keep the servo loop "critically damped" to prevent hunting or oscillating. During the time delay required for correction of the error current, the error voltage across the summing resistor 5 is compared to the reference voltage 8 in a fast and sensitive 2X amplifier 9 to initiate the alarm circuits.

Figure 1B:
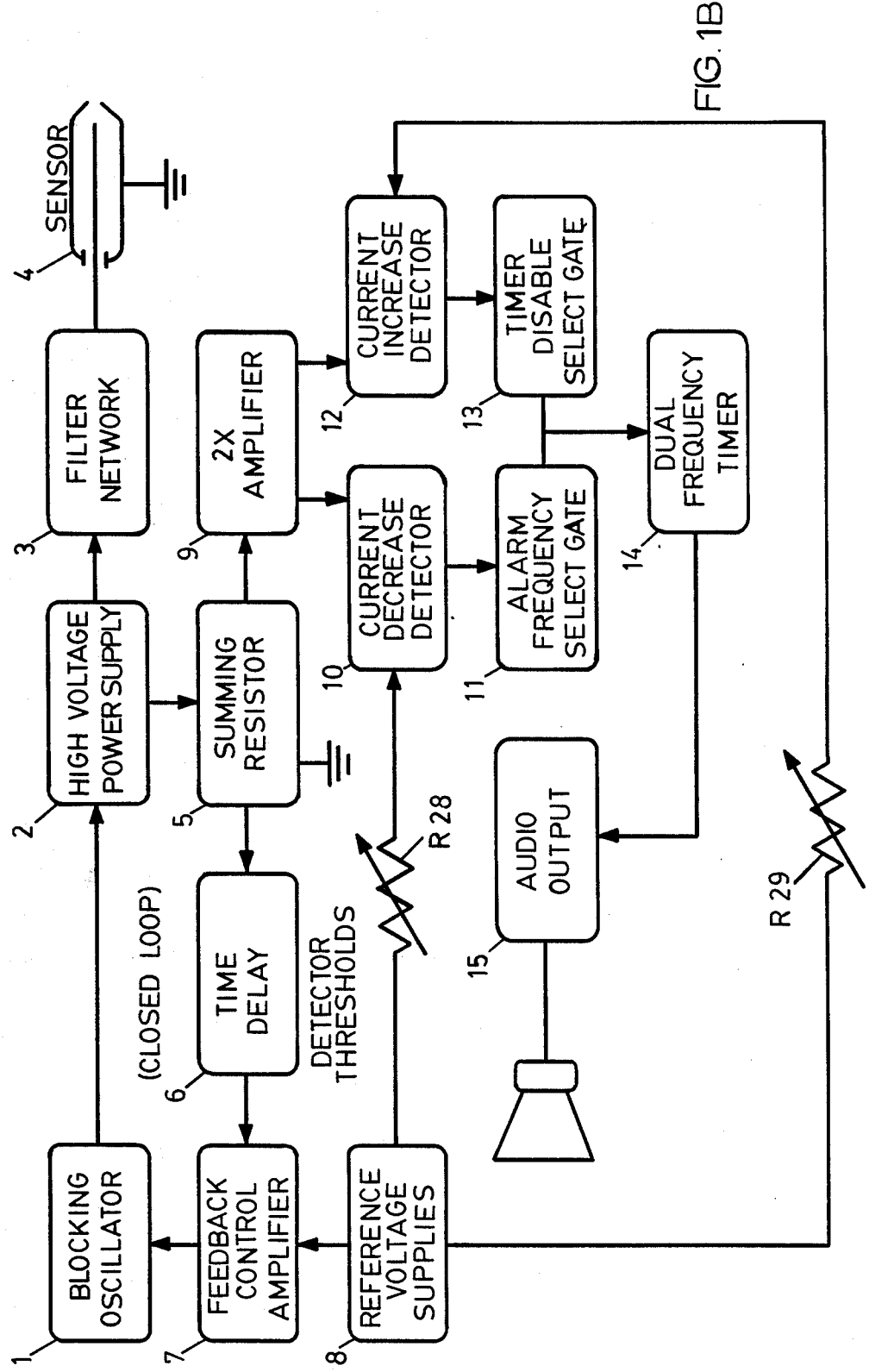
FIG. 1B is a block diagram of the embodiment of a self adjusting halogen gas leak detector in accordance with the invention.

With reference to FIG. 1B of the block diagram, the output of the 2X amplifier 9 is routed to the current decrease detector 10 and to the current increase detector 12. A decrease in the discharge current activates the alarm frequency select gate 11 which triggers the dual frequency timer 14 to jump from a fixed low frequency to a high fixed audio frequency which causes the audio output 15 to sound an alarm. An increase in the discharge current activates the timer disable select gate 13 which disables the dual frequency timer 14 stopping the low frequency output to the audio output 15. Thus, under static conditions a low frequency tick is heard at the audio output 15, an increase in discharge current stops the tick, and a decrease in discharge current causes a high frequency squeal at the audio output 15. Since sudden and significant changes in the discharge current are caused by the application of gaseous impurities to the sensor 4, the audio output 15 is a measure of the presence and direction of a gaseous leak.

The following are references on the block diagram, FIG. 1B, which do not appear in the above description of the preferred embodiment: Blocks 1, 2, 3, 5, 6, 7, 8 and resistors R28 and R29.

DETAILED DESCRIPTION OF THE ELECTRONIC CIRCUITRY

Figure 2:
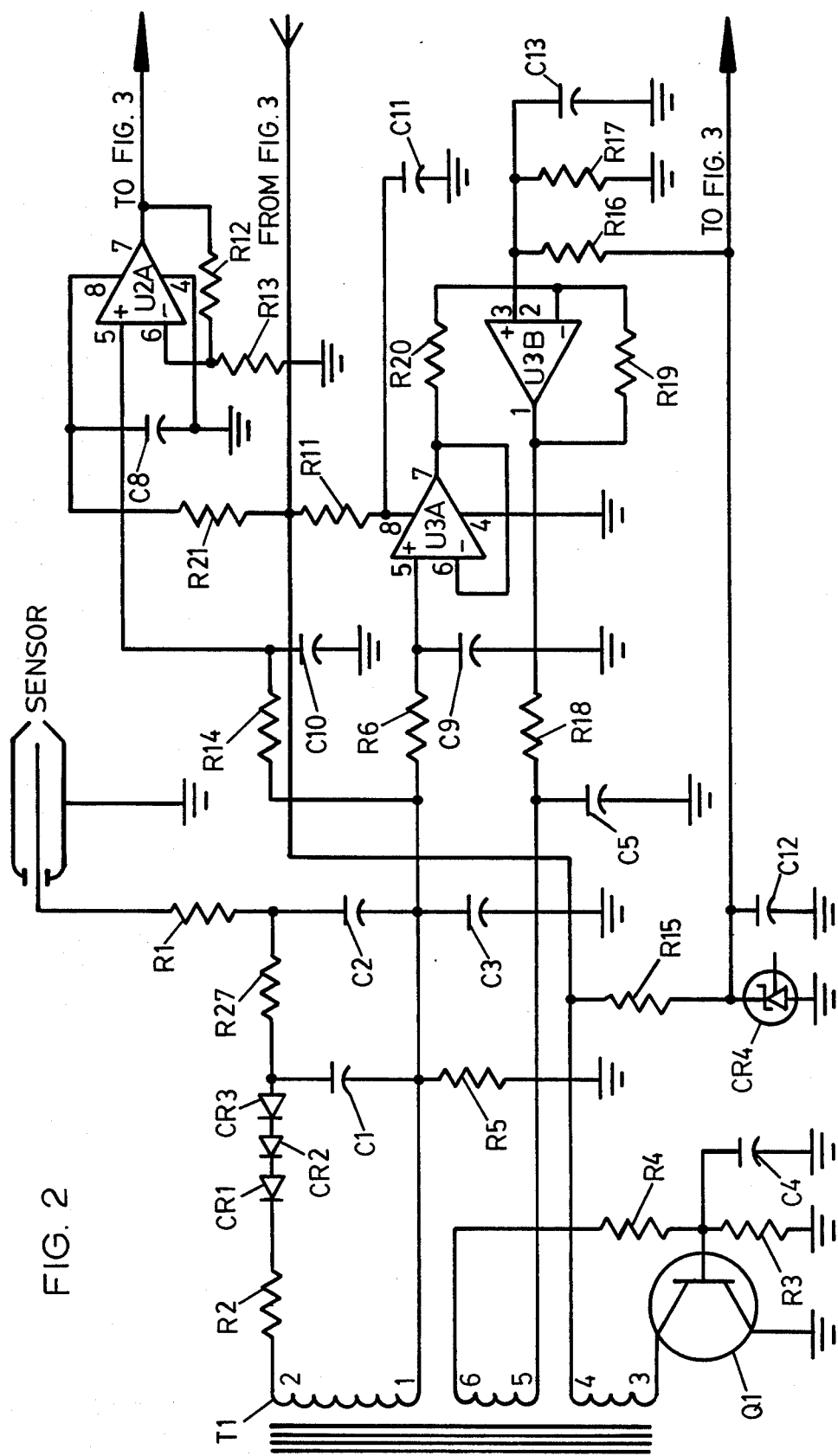
FIG. 2 is a schematic of the closed loop sensing circuits of the embodiment to the invention.

Referring to FIG. 2 in detail:

A high negative DC voltage required to establish a corona in the sensor tip is generated by a controlled blocking oscillator Q1 and the pulse forming transformer T1. The high voltage pulses at pin 2 of T1 are applied to R2, which limits peak current through the rectifiers CR1, CR2, and CR3 where the pulses are rectified to pass only a negative current to a PI type filter composed of C1, R27 and C2 to provide the negative current through R1 to the corona generating sensor tip. The shell of the sensor is connected to the common grounded bus. Pin 1 of T1 and the positive end of the PI filter capacitors C1 and C2 are connected to the summing resistor R5 to cause the current through the sensor to pass through R5. This causes R5 to develop a positive voltage with respect to ground proportional to the current through the sensor. Capacitor C3 maintains a constant voltage across R5 for small variations in the corona currents.

The voltage across the summing resistor R5 is applied to two circuits. The first is the control circuit for the blocking oscillator. The second is the detector circuit to indicate the presence of gaseous impurities in the atmosphere. In the first control circuit the voltage developed across the summing resistor R5 is applied through a large value resistor R6 to charge capacitor C9. This RC combination causes a delay time before a change in the voltage across R5 is applied to the control amplifier U3A. The voltage across C9 is applied to the non-inverting input of the operational amplifier U3A pin 5. The operational amplifier U3A has a gain of one and is used to isolate the voltage on C9 from the control circuit of operational amplifier U3B. Operational amplifier U3B having a gain of 10, inverts any changes in the delayed voltage from the summing resistor R5 and U3A, compares this voltage to a stable reference supplied by zener regulator CR4 and voltage divider resistors R16 and R17 applied to pin 3 of U3B, and applies this voltage through resistor R18 to the control winding pin 5 of transformer T1. This voltage is the feedback voltage, which is passed through the feedback winding of T1 pins 5 and 6 through current limiting resistor R4 and R3 to the base input of the power supply transistor Q1. This voltage controls the output level of the blocking oscillator and as such forms a closed loop feedback system to maintain the corona current through resistor R5 and the sensor at a stable constant level. Likewise any changes in the current through resistor R5 is inverted and applied through this feedback circuit to cause correction of the corona current to the initial preset value referenced to the stable reference voltage. Herein is the principal embodiment of this invention. In normal operation, feedback control systems must contain time delay elements which limit the speed of operation from the time an error voltage is detected until the time that the correction is applied. This delay time is just sufficient to permit the operation of an alarm circuit, which signals that an error voltage has been generated in the corona current. To obtain the voltage necessary for the alarm circuits, resistor R14 is connected to the summing resistor R5 and thence to the non-inverting input, pin 5 of the operational amplifier U2A which provides isolation from resistor R5 and amplifies the error voltage two times for proper operation of the alarm circuits.

Figure 3:
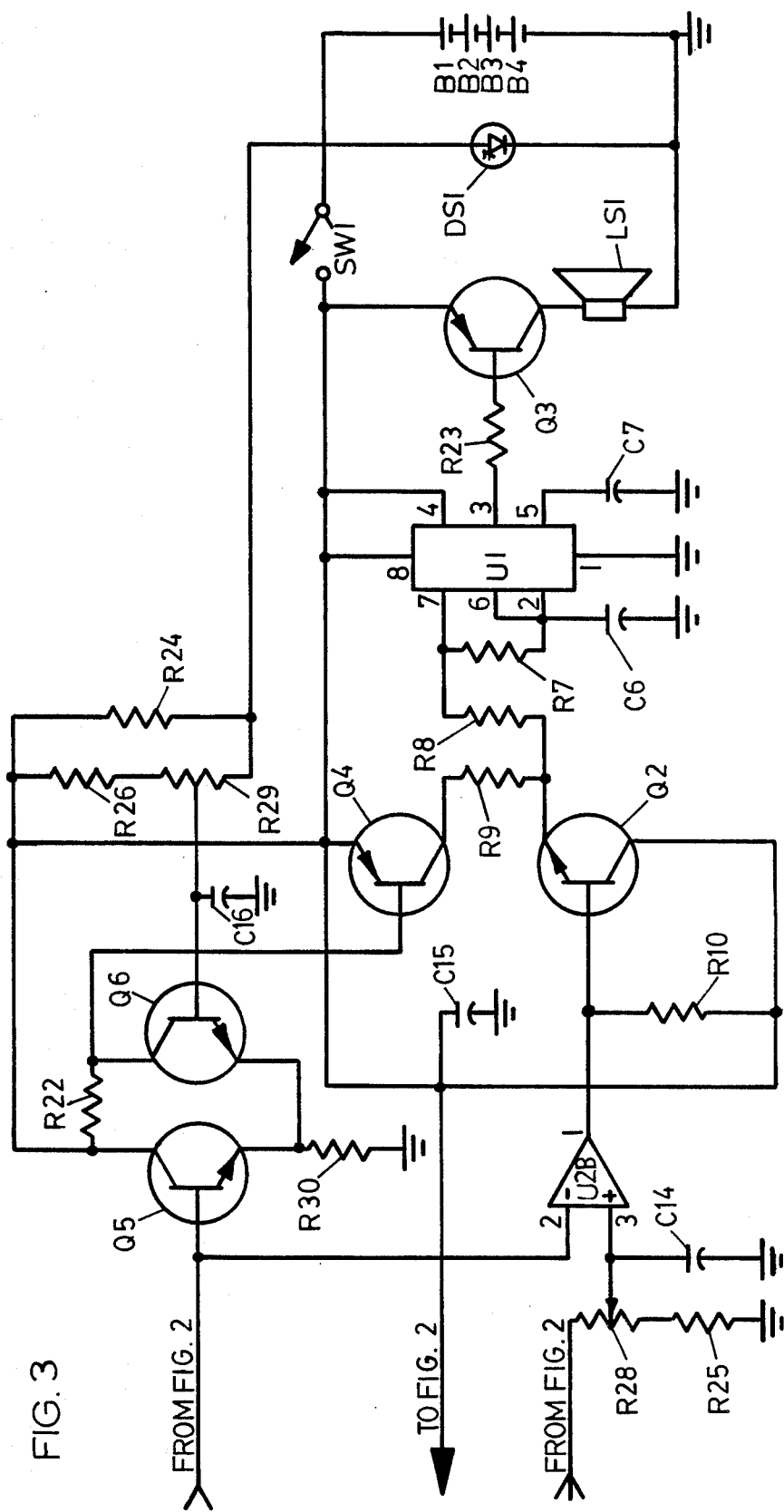
FIG. 3 is a schematic of the alarm, detection and power circuits of the embodiment of the invention.

Referring in detail to FIG. 3:

The alarm detection and power circuits of FIG. 3 operate as follows:

The error voltage from the operational amplifier U2A of FIG. 2 which has been amplified two times is applied to two separate alarm circuits; namely, operational comparator U2B and a dual transistor comparator Q5 & Q6. The error voltage applied to the inverting input, pin 2 of operational comparator U2B is compared with an adjustable level of the reference voltage. This alarm adjust level is set just below the fixed stable operating level of the summing voltage across resistor R5. Any increase in the summing voltage, which is a measure of an increase in corona current or likewise an increase in the gaseous impurity concentration will cause the output of the comparator U2B to go to a high voltage level. The output of comparator U2B drives the base of transistor Q2 into conduction which provides drive current to a timer circuit U1, which changes the time constant R8, R7, C6 of the timer U1 and causes a high frequency output at pin 3 of timer U1. The high frequency output of U1 is applied through audio drive transistor Q3 to loudspeaker LS1.

After the initial setup of said summing amplifier feedback circuit the output of the timer circuit U1 pin 3 is a short pulse caused by the time constant of resistors R7, R8, & R9 and capacitor C6 through the normally conducting transistor Q4 from the main supply voltage. Transistor Q4 is held in conduction by the base drive supplied from the collector resistor of voltage comparators Q5 & Q6, which compare the summing error voltage from resistor R5 with a mute adjust voltage preset to a level just above the fixed stable summing voltage across resistor R5. Any decrease in the summing voltage which constitutes a significant decrease in the corresponding corona discharge current and likewise a decrease in the gaseous impurity concentration of the atmosphere will cause the comparator Q5 & Q6 to cut off drive current to transistor Q4 which will prevent drive into the timing circuit U1 and mute the output of the loudspeaker.

Whenever any changes occur in the corona discharge current caused either by some changes in the components of the detecting apparatus or by a detection of a change in the gaseous impurity concentration of the atmosphere as detected by the disposed sensor, the error voltage generated at the summing resistor R5 starts to correct for this change in an effort to return the system to a stable operating condition. This correction is continually in operation even during the time that the error is detected and an alarm signal indicates that a change is occurring. The finite time between returning the system to a stable condition is used to indicate that a change has occurred in the discharge current. The signals provided by the alarm circuit are the steady tick audio output during stable operation, the high frequency squeal whenever an increase in the gaseous impurities is detected, and a muting of any audio output signal whenever a decrease in the gaseous impurities is detected. Between these three unique sounds the operator of the detector will be able to detect any significant changes in the gaseous impurity of the atmosphere and to locate leaks in halogen gaseous systems.

In the operation of the impurity detector of the present invention, normally, the detector is used in an environment which contains some background amounts of the impurities to be detected. Herein lies one of the problems associated with previous detectors; that is calibration and recalibration of the most sensitive operating condition of the instrument. When the detector of the present invention is first turned on, maximum corona discharge current is caused to flow until the atmosphere to which the sensor is exposed is sensed and the corona discharge current reaches a fixed balanced condition. Now any increase or decrease from the stable condition causes an error voltage in a closed loop servo system. This error voltage is detected and used to signal the increased or decreased level of the corona current which represents a change in the gaseous impurity level of the atmosphere. The error voltage is applied as a continuously correcting voltage to the corona current high voltage source to maintain the level at a fixed stable and sensitive level.

The above description should be considered exemplary and of the preferred embodiment only. Other modifications of the invention will occur to those who make and use the invention. It is desired to include within the scope of the present invention all such inventions which come within the scope and meaning of the appended claims.

The following are references on schematics which do not appear in the above detailed descriptions: Resistors; R10, R11, R12, R13, R15, R19, R20, R21, R22, R23, R24, R25, R26, R28, R29, R30. Capacitors; C4, C5, C7, C8, C10, C11, C12, C13, C14, C15, C16. Miscellaneous; Sensor, Swi, DS1, B1, B2, B3, B4.

The embodiment of the invention which is claimed as new and which an exclusive property or privilege is claimed is defined as follows:

1. Apparatus for detecting impurities in an atmosphere comprising:
   a sensor consisting of a pair of first and second electrodes disposable in the atmosphere, said first electrode comprising a cylindrical cavity therein, said cylindrical cavity having one open end for admitting atmosphere thereto and a central axis, said second electrode comprising a rigid needle-shaped projection disposed in said cavity and substantially in alignment with said central axis;
   a power supply means for establishing a corona discharge across said first and second electrodes in a continuous corona region, said power supply means consisting of a transistor, pulse transformer equipped with a feedback control winding, rectifier, filter and associated components;
   a summing resistor in series with the said first and second electrodes of the sensor and a power supply output terminal through which the said sensor corona discharge current flows in a closed loop;
   a reference voltage to establish a stable reference source;
   a feedback control circuit to sense the voltage across said summing resistor, condition the amplitude and timing of this voltage by comparison with the said reference voltage, establish a feedback error voltage which is applied to said feedback control winding of the pulse transformer in said power supply to cause the corona discharge of said sensor to remain relatively constant under all conditions;
   an error voltage amplifier, with a gain of two, connected to said summing resistor;
   first and second current detectors referenced to said reference voltage, the first to detect a decrease in the voltage at the said summing resistor and the second to detect an increase in the voltage at the said summing resistor in order to detect decreased or increased respective changes in the said sensor corona discharge current;
   first and second gating circuits controlled from said first and second detectors;
   a dual frequency timer controlled from the said first and second detectors and said gating circuits;
   an audio output and speaker controlled from the said dual frequency timer;
   thereby to detect and signal any significant changes in the corona discharge current of the said sensor which are direct indications of changes in the gaseous impurities of the sensed atmosphere.

* * * * *